United States Patent [19]

Disteldorf et al.

[11] Patent Number: 4,912,210

[45] Date of Patent: Mar. 27, 1990

[54] PROCESS FOR THE PREPARATION OF (CYCLO)ALIPHATIC URETEDIONES

[75] Inventors: Josef Disteldorf, Marl; Werner Huebel, Recklinghausen; Karl Schmitz, Gladbeck, all of Fed. Rep. of Germany

[73] Assignee: Huels Aktiengesellschaft, Marl, Fed. Rep. of Germany

[21] Appl. No.: 244,355

[22] Filed: Sep. 15, 1988

[30] Foreign Application Priority Data

Nov. 21, 1987 [DE] Fed. Rep. of Germany ....... 3739549

[51] Int. Cl.$^4$ .................. C07D 229/00; C07D 213/4
[52] U.S. Cl. .................................................. 540/202
[58] Field of Search ......................................... 540/202

[56] References Cited

FOREIGN PATENT DOCUMENTS 3420113 5/1985 Fed. Rep. of Germany .
1207673 10/1970 United Kingdom .

Primary Examiner—Mukund J. Shah
Assistant Examiner—C. L. Cseh
Attorney, Agent, or Firm—Oblon, Spivak, McClelland, Maier & Neustadt

[57] ABSTRACT

A process for the preparation of a uretedione, comprising the steps of:
  (i) reacting at least one $C_{6-15}$ (cyclo)aliphatic diisocyanate under substantially anhydrous conditions with a pyridine of the formula

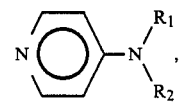

wherein $R_1$ and $R_2$ are, independent from one another, a $C_{1-4}$ alkyl group or $R_1$ and $R_2$ taken together with the attached nitrogen form a pyrrolidine, piperidine or morpholine ring, to form a reaction mixture containing said uretedione, and
  (ii) isolating said uretedione from said reaction mixture by vacuum thin layer evaporation after the degree of dimerization in said reaction mixture has reached 10–80%.

14 Claims, No Drawings

PROCESS FOR THE PREPARATION OF (CYCLO)ALIPHATIC URETEDIONES

BACKGROUND OF THE INVENTION

1. Field of the Invention

The invention is related to an improved process for the preparation of largely isocyanurate-free uretediones from (cyclo)aliphatic diisocyanates. Such uretediones can be processed into light-fast, single and two component polyurethane paints. The presence of isocyanurates is undesired in a number of applications since, as well-known, they are trifunctional and have a tendency to form crosslinkages. In practice an admixture of more than 0.5% is regarded as undesirable.

2. Discussion of the Background

In principle it is well-known that uretediones can be prepared in the presence of specific catalysts through dimerization of isocyanates. Previously for this purpose antimony pentafluoride, trialkylphosphines, amino-substituted phosphines, imidazoles, guanidines, and pyridines have been proposed.

The drawback in the use of antimony pentafluoride (cf. DE-OS No. 34 20 114) is that this corrosive and expensive compound must be destroyed prior to distillation with a five-fold quantity of zinc powder and the antimony and zinc fluoride precipitate must be removed by means of filtration.

A process is known from FR-PS No. 15 32 054 in which tertiary phosphines or boron trifluoride are added as dimerization catalysts. However, they catalyze not only the dimerization but also to a significant degree also the trimerization of isocyanates. In addition to this, due to its high corrosiveness, boron trifluoride can be added only when specific protective measures are taken.

1,2-Dimethylimidazole is an excellent dimerization catalyst for aromatic isocyanates (cf. Synthesis 1975, p. 463 ff.). However, in the case of isocyanates that do not have any aromatic NCO groups, this catalyst is clearly less selective. For example, when benzyl isocyanate is added, a mixture of 24% isocyanurate and only 76% uretedione is obtained.

In practice amino-substituted phosphines have prevailed as dimerization catalysts.

According to the process of DE-OS No. 30 30 513, the uretedione of the isophorone diisocyanate is prepared in the presence of an organic phosphorus-nitrogen-catalyst by means of dimerization of monomers and then distilled in a thin-layer evaporator. The uretediones remain in the distillation residue while the unconverted monomers with the majority of the added catalyst are collected as distillate, which is recycled into the process. Tris-(N,N-dimethylamino)-phosphine (PTD) is designated as the preferred catalyst. Uretediones, which were produced in the presence of PTD, contain typically 1% isocyanurate, 1% monomers, and 0.01–0.1% catalyst.

In the DE-OS No. 34 47 635 it is proposed that for the dimerization of organic isocyanates the same type of catalysts be used with concurrent use of active hydrogen containing organic compounds such as alcohols, phenols, (cyclo)aliphatic amines, amides, urethanes, and ureas. PTD and tris-(N,N-diethylamino)-phosphine are particularly preferred catalysts. If di- or higher functional isocyanates are added, the reaction usually stops after attaining a degree of dimerization ranging from 10 to 50% due to the addition of a catalyst poison such as chloroacetic acid (cf. page 16, first paragraph). Isolating the uretedione presents a problem. Under the conditions of thin-layer evaporation there is the risk of a catalyzed dissociation of the uretedione that is present back to the original isocyanates (cf, page 16, middle). If the catalyst with the excess isocyanate can be removed by means of distillation, deactivation of the catalyst is superfluous. However, then uncontrollable secondary reactions can occur during and after work-up (cf, page 20).

It is known that PTD has a tendency to react in the presence of atmospheric oxygen to form hexamethyl triamidophosphoric acid, which as is well-known, is suspected to be a carcinogen (cf. Br.J.Cancer 38, 418–427 (1978)). Therefore, the use of PTD should be avoided. In addition to this, the aforementioned processes have the drawback that the catalysts enter into secondary reactions and thus are partially consumed. Therefore, in these processes, the lost catalyst must be regularly replaced. In the latter processes, a significant proportion of the catalyst thus employed remains in the uretedione after the deactivation. Therefore, a drawback of both processes is the high cost of the catalyst.

Other dimerization catalysts are also known from the literature. For example, in the JP-AS No. 71/37 503 the dimerization of 2,4-toluylene diisocyanate with cyclic amidines such as 1,8-diazabicyclo[5.4.0]undec-7-en is described. Experiments conducted by the Applicant show that (cyclo)aliphatic diisocyanates cannot be dimerized with this catalyst (see reference example A). Apparently the well-known, low reactivity of these diisocyanates is inadequate to facilitate a reaction.

The object of DE-PS No. 10 81 895 (corresponding to U.S. Pat. No. 3,144,452) is a process for the preparation of N,N-diaryluretediones and triarylisocyanurate acid esters through di- or trimerization of aromatic isocyanates. Pyridines containing a substituent in the 3- or 4-position and of a specified basicity are used as catalysts. Among other things, 4-aminopyridines that are substituted by means of alkyl groups are mentioned. According to this process, it is apparently possible to obtain uretediones, isocyanurates or their mixtures, depending on the quantity of the catalyst, the reaction temperature, and type of solvent that is used. Thus, for example, it is recommended that for the production of uretediones the catalyst be added in a quantity ranging from 0.005 to 15%, with respect to the weight of the isocyanate added, the mixture be reacted at the lowest temperature possible, and an inert organic solvent be used in which the uretedione dissolves poorly.

The fact that the quantity of catalyst recommended for the preparation of isocyanurates overlaps in broad ranges the aforementioned data and the other two reaction parameters are also not clearly delineable, leads one skilled in the art to doubt the possibility of controlling a selective reaction. Reference experiments conducted by the Applicant show in fact that the two oligomers are always formed. For example, in the follow-up of Example 2, 2% by weight of isocyanurate was obtained. If the reaction mixture is heated briefly to 145° C., even 10% by weight of isocyanurate is obtained, whereas at the same time the uretedione is partially split into the monomer.

It is evident from a later application of the patent holder that 4,4'-diphenylmethane-diisocyanate is trimerized in the presence of 4-dimethylaminopyridine at room temperature and is converted to higher oligomeric products (cf. DE-AS No. 16 94 485). From this, too, it can be inferred that apparently the pyridine derivatives always catalyst both reactions—the dimerization and the trimerization. Therefore, pyridine derivatives do not seem to be suitable for the preparation of uretediones, which should be almost free of isocyanurates. In particular, this applies to aliphatic isocyanates, since in contrast to the aromatic isocyanates, they form either no uretediones or only when special reaction conditions are maintained are they in a position to form the dimeric addition products (cf. J.Org.Chem. 36, 3056 (1971)).

Therefore, whereas numerous processes for the dimerization of aromatic diisocyantes are known, there is practically only one possibility for dimerizing (cyclo)aliphatic diosocyanates; and it is based on the use of undesired aminophosphines (see DE-OS No. 34 37 635)).

The process described in JP-OS No. 84/98180 for the oligomerization of (cyclo)aliphatic diisocyanates is not suitable for the targeted preparation of uretediones, since it is known that the mixtures obtained comprising uretediones and isocyanurates are separable only with great difficulty. Uretediones have the tendency, on heating to reseparate back into their original components. In particular, this can be expected when catalyst residues are still present.

SUMMARY OF THE INVENTION

Thus one object of the present invention is to provide a process for catalytic preparation of (cyclo)aliphatic uretediones with more than 99% purity, which is independent of the use of expensive and potentially carcinogen aminophosphines.

This and other objects which will become apparent from the following specification have been achieved by the present process for the preparation of a uretedione which comprises the steps of:

(i) reacting at least one $C_{6-15}$ (cyclo)aliphatic diisocyanate under substantially anhydrous conditions with a pyridine of the formula

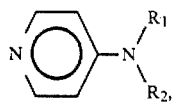

wherein $R_1$ and $R_2$ are, independently from one another, a $C_{1-4}$ alkyl group or $R_1$ and $R_2$ taken together with the attached nitrogen form a pyrrolidine, piperidine or morpholine ring, to form a reaction mixture containing said uretedione, and (ii) isolating said uretedione from said reaction mixture by vacuum thin layer evaporation after the degree of dimerization in said reaction mixture has reached 10-80%.

DETAILED DESCRIPTION OF THE PREFERRED EMBODIMENTS

Surprisingly, such a process has now been found. It comprises dimerizing an aliphatic and/or cycloaliphatic diisocyanate containing 6 to 15 carbon atoms in the presence of a pyridine of the general formula:

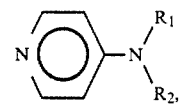

in which $R_1$ and $R_2$ denote independently from one another an alkyl group having 1 to 4 carbon atoms or together with the nitrogen can form a pyrrolidine ring, piperidine ring, or a morpholine ring; and after reaching a degree of dimerization of 10 to 80%, preferably 20 to 60%, the reaction mixture is subjected to vacuum thin-layer evaporation in order to isolate the uretedione. Thus, it is not necessary to stop the reaction by adding a catalyst poison. Isophorone diisocyanate is preferred as a diisocyanate. The substituted pyridine, in particular p-dimethylaminopyridine, is added in a quantity ranging from 0.05 to 10% by weight, preferably from 0.2 to 5% by weight. Dimerization is preferably performed at a temperature between 0° to 100° C., the thin-layer evaporation depending on the attached vacuum ranging from 0.1 to 20 mbar at a temperature from 150° to 190° C. The distillate of the thin-layer evaporation can be recycled again. It is preferable that the dimerization be performed in the presence of an inert protective gas to provide an anhydrous atmosphere.

Thus of the substituted pyridines disclosed in DE PS No. 10 81 895, only the 4-dialkylaminopyridines are suitable as dimerization catalysts. Based on prior art, it is surprising that these pyridines are highly selective catalysts for the dimerization of (cyclo)aliphatic diisocyanates.

It is remarkable that according to this process uretediones are obtained in high purity. On the basis of prior art reference one would have expected that during the reaction a specific proportion of isocyanurates would already be formed. The vacuum thin-layer evaporation requires only a short period of time at temperatures up to a maximum of 190° C. Even under these temperature conditions which, for uretediones are drastic, no significant quantity of isocyanurates is formed. In the process of the invention the total percentage of isocyanurate formed is thus below 0.5%, with respect to the total quantity of uretedione produced at the same time.

It is also advantageous that the substituted pyridines that are required as catalysts are readily available commercial products.

Finally, the course of the reaction is significantly easier to control with the use of substituted pyridines since almost no secondary reactions take place.

By "(cyclo)aliphatic" is meant aliphatic and cycloaliphatic diisocyanates having 6 to 15 carbon atoms, preferably 8 to 12 carbon atoms. For example, hexamethylene diisocyanate, dodecamethylene diisocyanate and bis(4-isocyanatocyclohexyl)-methane and their mixtures are suitable for use as the diisocyanates. Preferred aliphatic diisocyanates are 2-methylpentamethylene diisocyanate, as well as 2,2,4- and 2,4,4-trimethylhexamethylene diisocyanate. Among the cycloaliphatic diisocyanates, isophorone diisocyanate is preferred.

The pyridine used as dimerization catalyst has the general formula:

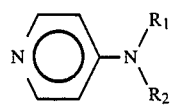

$R_1$ and $R_2$ denote, independently of one another, an alkyl group having 1 to 4 carbon atoms or together with the neighboring nitrogen atom form a pyrrolidine, piperidine, or morpholine ring. Excellent results are achieved with p-pyrrolidinopyridine (see Tables 4 and 5). However, due to their better availability, 4-dimethylaminopyridine and/or 4-diethylaminopyridine are preferred as catalysts. The catalyst is added in a quantity ranging from 0.5 to 10%, in particular from 0.2 to 5%, with respect to the parts by weight of the diisocyanate added.

The dimerization can be performed in the presence of solvents, which are inert with respect to diisocyanates. Of course, as a rule such a variation of the process does not exhibit any special advantages. In particular hexane, toluene, xylene, chlorobenzene and their mixtures are suitable.

The reaction temperature normally ranges from about 0° to 100° C., preferably from about 20° to 80° C. It is advantageous to perform the dimerization in the presence of a protective inert gas atmosphere such as nitrogen, argon, etc. to provide substantially androus conditions. The reaction may be carried out at normal atmospheric pressure. The reaction times generally range from 1 to 5 days, and depend primarily on the concentration of the catalyst.

As soon as a degree of dimerization has reached from 10 to 80%, preferably from 20 to 60%, the reaction feedstock is subjected directly to a vacuum thin-layer evaporation. Thus it is advantageous to forego the deactivation of the catalyst. With thin-layer evaporation for the purpose of preparing IPDI uretedione, the temperature is set, in particular, at 180° C. and the pressure is set at 0.55 mbar in the preevaporator. In the main evaporator the temperature is, in particular, 165° C. and the pressure is 0.05 mbar. The dwell time in the preevaporator and the main evaporator is then approximately 1 minute respectively.

In the vacuum thin-layer evaporator more than 99% pure uretedione is recovered as the distillation residue. The monomer content is determined by means of gas chromatography. The final product contains less than 0.5% isocyanurate; the monomer content is below 0.4%; catalyst residues are not detectable.

The distillate comprises monomer diisocyanate and catalyst. It is preferable to recycle the distillate to the dimerization process.

The degree of dimerization was determined using the NCO number and the course of the reaction was observed with the aid of the NCO number. The NCO number is determined according to the method described in Houben-Weyl "Methoden der Organischen Chemie", Vol. 14/2, Stuttgart (1963), p. 85.

The isocyanurate content in the reaction product is determined qualitatively using IR spectroscopy and quantitatively by determining the thermal value of NCO. In order to determine the thermal value of NCO, the sample is boiled in dichlorobenzene for 2 hours. Then the NCO number is determined in the conventional manner.

Having generally described this invention, a further understanding can be obtained by reference to certain specific examples which are provided herein for purposes of illustration only and are not intended to be limiting unless otherwise specified.

EXAMPLES

EXAMPLE 1

A 100 g sample of a (cyclo)aliphatic diisocyanate, which contains 1% by weight of p-dimethylaminopyridine, was maintained at 70° C. under nitrogen for 24 hours. Then the degree of dimerization was determined. Table 1 shows the values which were obtained.

TABLE 1

| (Cyclo)aliphatic diisocyanate | Degree of Dimerization |
|---|---|
| 2-methylpentane-1,5-diisocyanate | 33.8% |
| isomer mixture comprising 2,2,4- and 2,4,4-trimethylhexamethylene diisocyanate | 25.6% |
| hexane-1,6-diisocyanate | 29.9% |
| isophorone diisocyanate | 26.6% |

EXAMPLE 2

100 g Samples of isophorone diisocyanate, which contain varying quantities of p-dimethylaminopyridine, were left standing at room temperature under nitrogen for 1 to 5 days. Then the degree of dimerization was determined, as shown in Table 2.

TABLE 2

| Example | Parts by weight of p-dimethylamino-pyridine (%) | Degree of dimerization | |
|---|---|---|---|
| | | after 1 day | after 5 days |
| 2.1 | 0.5 | 11.1% | 33.3% |
| 2.2 | 1.0 | 28.6% | 49.2% |
| 2.3 | 2.0 | 33.9% | 61.9% |
| 2.4 | 5.0 | 55.0% | 74.1% |

EXAMPLE 5

Samples of isophorone diisocyanate, which contain varying parts by weight of p-dimethylaminopyridine, were left standing at room temperature under nitrogen. Then distillative work-up was performed in a vacuum thin-layer evaporator. Table 3 shows the test results that were obtained.

TABLE 3

| | Example 3.1 | Example 3.2 | Example 3.3 |
|---|---|---|---|
| isophorone diisocyanate feedstock (kg) | 2.97 | 2.94 | 2.85 |
| p-dimethylaminopyridine (% by wt.) | 1.0 | 2.0 | 5.0 |
| reaction time (hours) | 120 | 67 | 17.5 |
| distillate (% by weight of feedstock) | 57.3 | 58.2 | 63.1 |
| uretedione yield (% by weight of feedstock) | 42.7 | 41.8 | 36.9 |

EXAMPLE 4

A 100 g sample of isophorone diisocyanate, which contains 5% by weight of dimerization catalyst, was maintained at room temperature under nitrogen for 1 day. Then the degree of dimerization was determined, as shown in Table 4.

TABLE 4

| Example | Catalyst | Degree of Dimerization |
|---|---|---|
| 4.1 | p-pyrrolidinopyridine | 61.4% |
| 4.2 | p-diethylaminopyridine | 55.0% |
| 4.3 | p-piperidinopyridine | 50.3% |
| 4.4 | p-morpholinopyridine | 16.9% |

EXAMPLE 5

A 100 g sample of isophorone diisocyanate, which contains 1% by weight of dimerization catalyst, was maintained at room temperature under nitrogen for 2 days. Then the degree of dimerization was determined, as shown in Table 5.

TABLE 5

| Example | Catalyst | Degree of Dimerization |
|---|---|---|
| 5.1 | p-pyrrolidinopyridine | 48.1% |
| 5.2 | p-diethylaminopyridine | 48.1% |
| 5.3 | p-dimethylaminopyridine | 39.7% |
| 5.4 | p-piperidinopyridine | 30.2% |

Reference Examples A to D

A 100 g sample of isophorone diisocyanate, which contains 1% by weight of dimerization catalyst, was maintained at room temperature under nitrogen for 1 to 10 days. Then the degree of dimerization was determined, as shown in Table 6.

TABLE 6

| Reference Example | Catalyst | Degree of Dimerization | |
|---|---|---|---|
| | | 1 day | 10 days |
| A | 1,8-diazabicyclo[5.4.0]-undec-7-ene | 0 | 0 |
| B | 1,2-dimethylimidazole | 0 | 0 |
| C | 3-dimethylaminopyridine | 0 | 0 |
| D | 2-dimethylaminopyridine | 0 | 0 |

Obviously, numerous modifications and variations of the present invention are possible in light of the above teachings. It is therefore to be understood that within the scope of the appended claims, the invention may be practiced otherwise than as specifically described herein.

What is new and desired to be secured by letters patent of the United States is:

1. A process for the preparation of a uretedione, consisting essentially of the steps of:
   (i) reacting a $C_{6\text{-}15}$ (cyclo)aliphatic diisocyanate under substantially anhydrous conditions with a pyridine of the formula wherein said pyridine is used in a quantity ranging from 0.05–10% by weight relative to the diisocyanate wherein $R_1$ and $R_2$ are, independently from one another, a $C_{1\text{-}4}$ alkyl group or $R_1$ and $R_2$ taken together with the attached nitrogen form a pyrrolidine, piperidine or morpholine ring, to form a reaction mixture containing said uretedione, and (ii) isolating said uretedione from said reaction mixture by vacuum thin layer evaporation after the degree of dimerization in said reaction mixture has reached 10–80%.

2. The process of claim 1, wherein said uretedione isolated from said reaction mixture is more than 99% pure.

3. The process of claim 1, wherein said isolating step is conducted after the degree of dimerization in said reaction mixture has reached 20–60%.

4. The process of claim 1, wherein 0.2–5% by weight of said pyridine is used.

5. The process of claim 1, wherein $R_1$ and $R_2$, independently, are a methyl or ethyl group.

6. The process of claim 1, wherein said reacting step is conducted at a temperature from about 0°–100° C.

7. The process of claim 6, wherein said reacting step is conducted at a temperature from about 20°–80° C.

8. The process of claim 1, wherein said vacuum thin layer evaporation is performed at a vacuum ranging from about 0.1 to 20 mbar and at a temperature ranging from 150°–190° C.

9. The process of claim 1, wherein the distillate obtained by said vacuum thin layer evaporation comprises said diisocyanate and said pyridine and wherein said distillate is recycled to said reacting step.

10. The process of claim 1, wherein said reacting step is conducted in inert gas atmosphere.

11. The process of claim 1, wherein said diisocyanate is a $C_{8\text{-}12}$ (cyclo)aliphatic diisocyanate.

12. The process of claim 1, wherein said diisocyanate is selected from the group consisting of hexamethylene diisocyanate, dodecamethylene diisocyanate, bis(4-isocyanatocyclohexyl)-methane, 2-methylpentamethylene diisocyanate, 2,2,4-trimethylhexamethylene diisocyanate, 2,4,4-trimethylhexamethylene diisocyanate and isophorone diisocyanate.

13. The process of claim 1, wherein said diisocyanate is isophorone diisocyanate.

14. The process of claim 1, wherein said reacting step is conducted in the presence of an inert solvent.

* * * * *